(12) United States Patent
Shelchuk

(10) Patent No.: US 6,970,744 B1
(45) Date of Patent: Nov. 29, 2005

(54) BIOENERGY GENERATOR

(75) Inventor: Anne M. Shelchuk, San Rafael, CA (US)

(73) Assignee: Pacesetter, Inc., Sylmar, CA (US)

(*) Notice: Subject to any disclaimer, the term of this patent is extended or adjusted under 35 U.S.C. 154(b) by 247 days.

(21) Appl. No.: 10/640,832

(22) Filed: Aug. 13, 2003

(51) Int. Cl.⁷ .................................................. A61N 1/18
(52) U.S. Cl. ............................................ 607/35; 429/2
(58) Field of Search ............................ 607/35, 34, 61, 607/1, 2; 429/2

(56) References Cited

U.S. PATENT DOCUMENTS

| | | | |
|---|---|---|---|
| 3,486,506 A | * 12/1969 | Michel | ............................ 607/19 |
| 3,861,397 A | 1/1975 | Rao et al. | ................ 128/419 B |
| 3,941,135 A | 3/1976 | Von Sturm et al. | ..... 128/419 PS |
| 4,294,891 A | 10/1981 | Yao et al. | ........................ 429/2 |
| 4,712,555 A | 12/1987 | Thornander et al. | ... 128/419 PT |
| 4,788,980 A | 12/1988 | Mann et al. | ........... 128/419 PG |
| 4,940,052 A | 7/1990 | Mann et al. | ........... 128/419 PG |
| 4,944,298 A | 7/1990 | Sholder | ................. 128/419 PT |
| 5,466,254 A | 11/1995 | Helland | ....................... 607/123 |
| 5,476,483 A | 12/1995 | Bornzin et al. | ................ 607/17 |
| 6,314,323 B1 | 11/2001 | Ekwall | .......................... 607/23 |

OTHER PUBLICATIONS

Ricky K. Soong et al., "*Powering an Inorganic Nanodevice with a Biomolecular Motor*," SCIENCE, vol. 290, pp 1555-1558 (Nov. 24, 2000).

* cited by examiner

*Primary Examiner*—Jeffrey R. Jastrzab
*Assistant Examiner*—Alyssa M. Alter

(57) ABSTRACT

A biogenerator, having a biomotor portion and a generator portion, suitable for use with, in and/or as an implantable device. A method of inducing an electromagnetic force in a coil using a biomotor.

19 Claims, 13 Drawing Sheets

EXEMPLARY BIOGENERATOR

BIOENERGY GENERATOR

TECHNICAL FIELD

Exemplary methods, systems and/or devices presented herein generally relate to bioenergy generators or "biogenerators" suitable for use in implantable devices.

BACKGROUND

Implantable devices often have limited electrical power supply; thus, a need exists for new sources of electrical power.

SUMMARY

An exemplary biogenerator includes a biomotor portion and a generator portion and is suitable for use with, in and/or as an implantable device. An exemplary method includes inducing an electromagnetic force in a coil using a biomotor.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary bioenergy generators are disclosed herein. The bioenergy generators are suitable for use in implantable stimulation devices and, in particular, stimulation devices capable of stimulating muscle and/or nerve tissue. In general, a bioenergy generator includes a "biomolecular motor" portion and an electric generator portion. Details of exemplary bioenergy generators are described below after a brief description of exemplary implantable stimulation devices.

Exemplary Stimulation Device

Various exemplary bioenergy generators and/or methods are optionally implemented in connection with any stimulation device that is configured or configurable to stimulate nerves and/or stimulate and/or shock a patient's heart.

Figure 1:
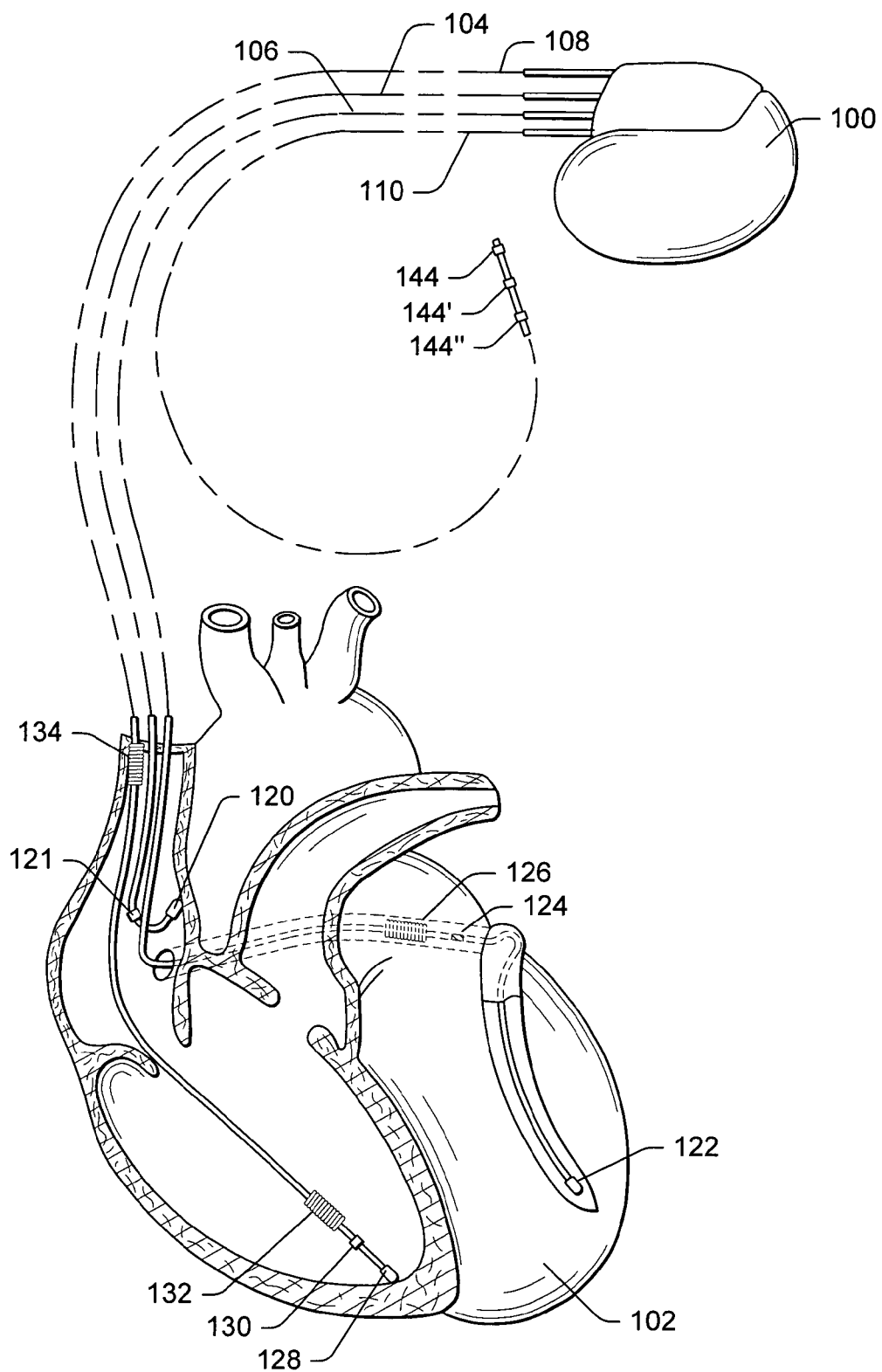
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
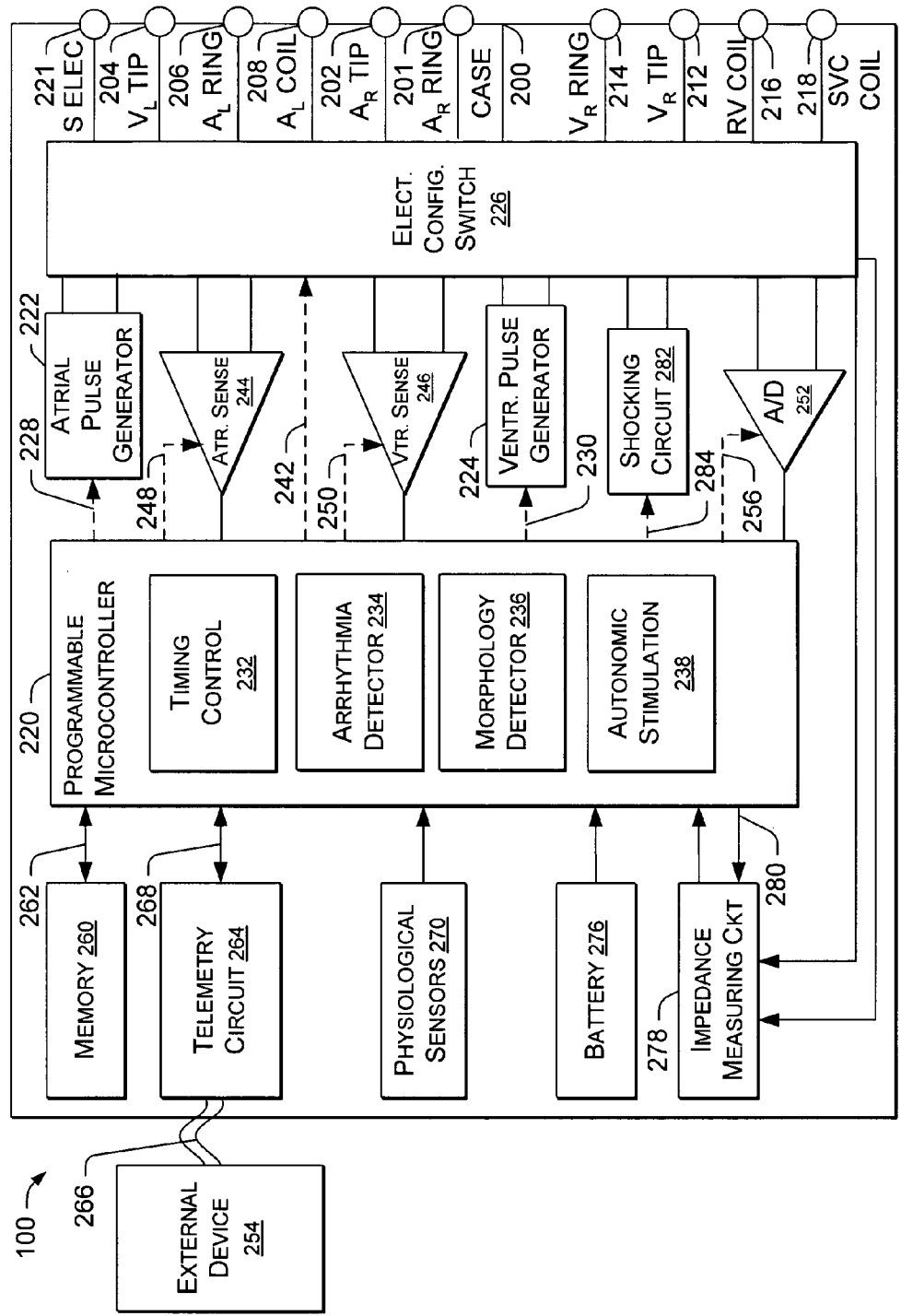
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Exemplary Bioenergy Generators or Biogenerators

Figure 3:
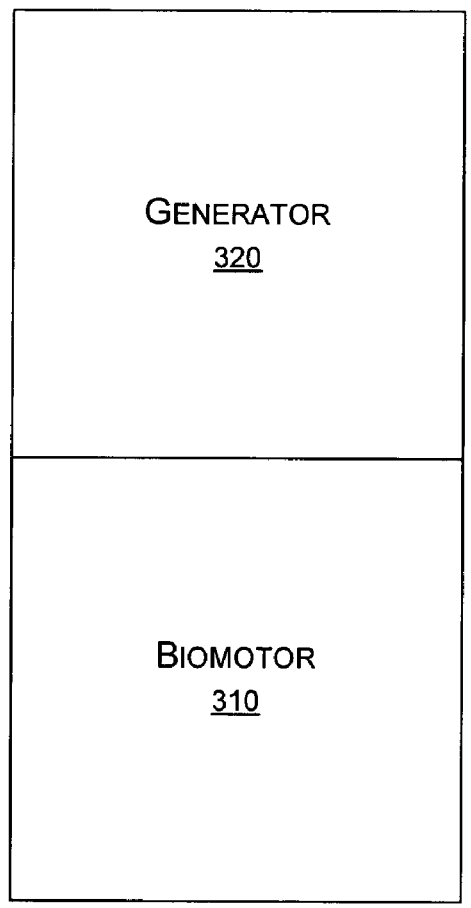
FIG. 3 is a block diagram of an exemplary biogenerator having a biomotor portion and a generator portion.

As already mentioned, various exemplary bioenergy generators or "biogenerators" include a biomolecular motor or "biomotor" portion and an electrical generator portion. Referring to FIG. 3, an exemplary biogenerator 300 is shown. The biogenerator 300 includes a biomotor portion 310 and a generator portion 320. Details of these two portions are described below.

Exemplary Biomolecular Motors

Various biomolecular motors are disclosed in an article by Soong, et al., "Powering an inorganic nanodevice with a biomolecular motor", Science, 209: 1555–1557 (2000), which is incorporated by reference herein. In particular, Soong, et al., discuss nanoscale devices that integrate biological molecules with nanofabricated structures. Soong, et al., discuss a biomolecular motor that relies in part on the enzyme F1-ATPase, which has dimensions of approximately 8 nm in diameter and approximately 14 nm length.

For inorganic components Soong, et al., used advanced electron-beam (e-beam) lithographic techniques which can provide components having sizes compatible with the scale of the F1-ATPase enzyme. Soong, et al., also used nickel as an interfacing metallic material because it can preferentially bind to histidine-tagged biomolecules. Soong, et al., reported that nickel pillars or supports, on which the F1-ATPase motor were attached, facilitated rotary motion by reducing drag force associated with the medium near the substrate surface. Further, the base of the pillars or supports was formed through silicon dioxide ($SiO_2$) deposition and subsequent patterning through reactive ion etching. Soong, et al., constructed Ni tips through e-beam lithography to form dots patterns on resist wherein metallic deposition and lift-off left the remaining Ni post or support tops. Soong, et al., also fabricated nickel rods on a separate, silicon substrate that were subsequently lifted-off and collected in solution. Treatment of a glass coverslip with buffer solutions containing motors and rods resulted in single molecule attachment to patterned post structures.

Soong, et al., successfully demonstrated anti-clockwise rotation of a nanofabricated nickel rod. For example, according to Soong, et al., upon introduction of a bioenergy source (e.g., 2 mM ATP), a nickel rod attached to an F1-ATPase enzyme rotated with a mean velocity of approximately 4.8 revolutions-per-second and a mean torque of approximately 19.5 pN·nm with approximately 50% efficiency.

Figure 4:
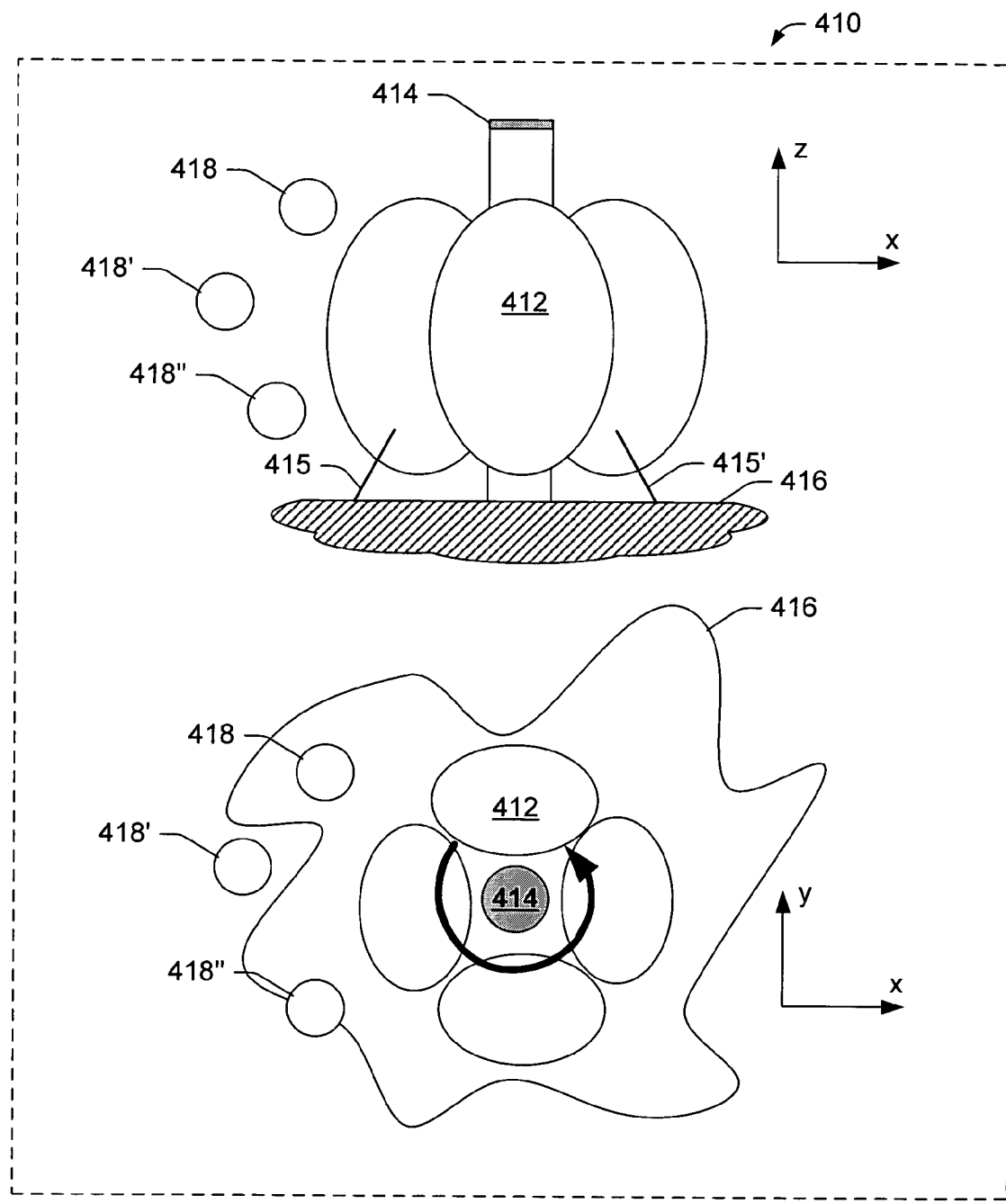
FIG. 4 is an approximate diagram of an exemplary biomotor.

Referring to FIG. 4, a side view (z-x plane) and a top view (y-x plane) of an exemplary biomotor 410 are shown. The biomotor 410 includes a biological motor 412, a cap 414, one or more tags 415, 415', a support 416, and a bioenergy source 418, 418', 418". For example, F1-ATPase optionally serves as the biological motor 412, a biotinylated cysteine optionally serves as the cap 414, histidine optionally serves as a tag 415, 415', nickel optionally serves as a support 416, and ATP optionally serves as a bioenergy source 418, 418', 418". In this example, (e.g., see Soong, et al.) hydrolysis of the bioenergy source causes an anti-clockwise rotation of the motor.

As described herein, various exemplary biogenerators include a biomotor, such as, but not limited to, those disclosed in the aforementioned article by Soong, et al. (2000). For example, in various exemplary biogenerators, the "rod" of Soong, et al., is replaced with one or more magnets and/or one or more coils.

Of course, other biomotors are also optionally suitable for use with generators disclosed herein. For example, a number of enzymes such as, but not limited to, kinesin, RNA polymerase, myosin, adenosine triphosphate (ATP) synthase and/or genetically modified variants thereof can optionally function as linear or rotary biological motors.

Exemplary Electric Generators

Electric generators, such as the generator 320 of FIG. 3, convert energy from a mechanical form to an electric form via a process known generally as electromechanical energy conversion. According to Faraday's law of electromagnetic induction, an electromotive force (emf) can be induced in a coil (or winding) by exposing the coil to a varying magnetic field and/or by moving the coil in a magnetic field. A typical configuration includes a static portion and a rotating portion. For example, an emf is induced in a coil by rotating the coil (e.g., rotor) in the magnetic field of a static magnet (e.g., stator). Similarly, an emf is also induced in a coil (e.g., stator) exposed to a time-varying magnetic field produced by, for example, a rotating magnet (e.g., rotor).

Figure 5:
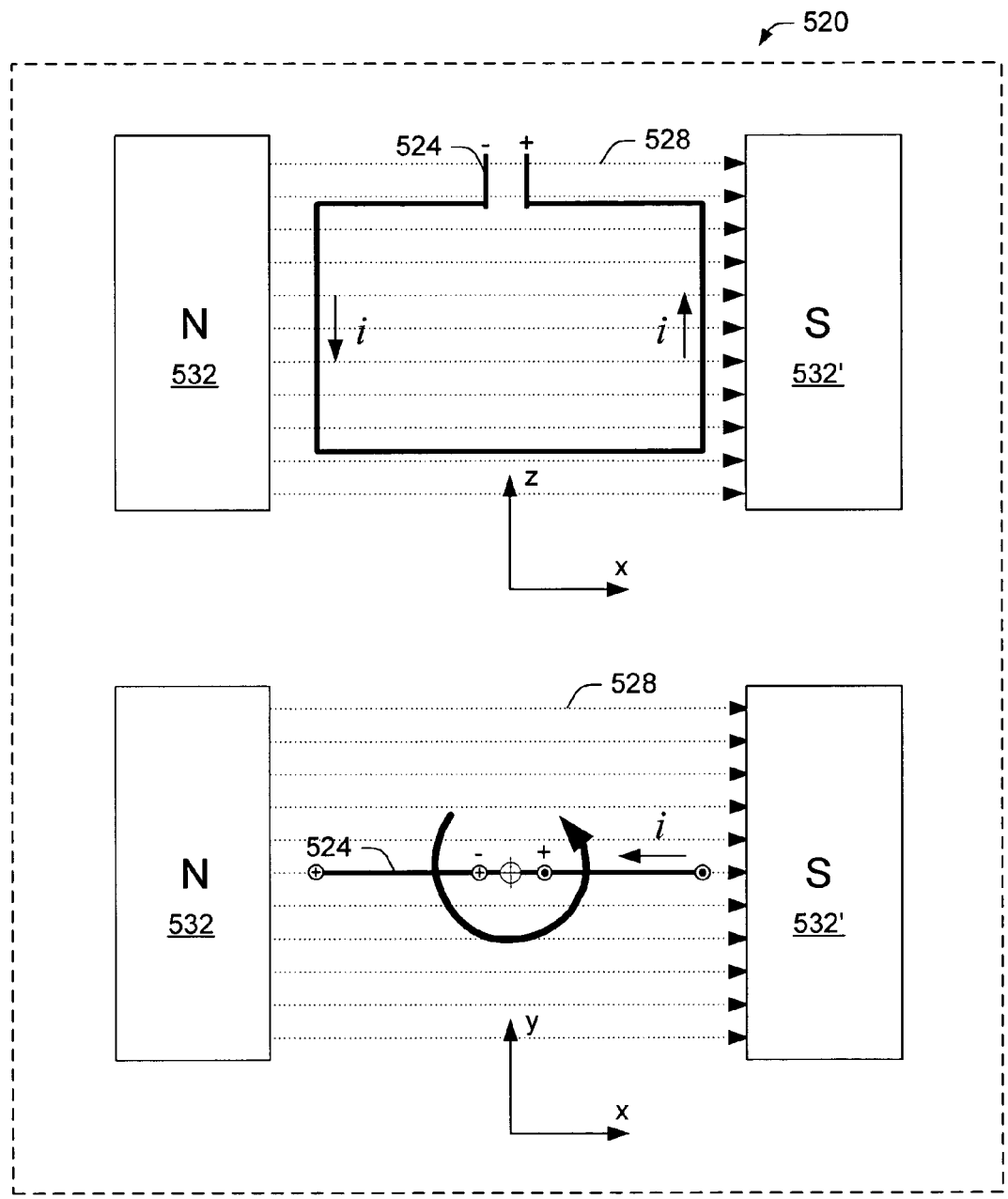
FIG. 5 is an approximate diagram of a rotating coil generator for use with a biomotor.

Referring to FIG. 5, a side view (e.g., z-x plane) and a top view (e.g., x-y plane) of an exemplary generator 520 are shown. Both views include a coil 524 and a magnetic field 528 associated with a dipole magnet having a north pole 532 and a south pole 532'. According to this exemplary generator 520, the coil 524 serves as a rotor while the dipole magnet (e.g., poles 532, 532') serves as the stator. The coil 524 intersects the magnetic field 528 at approximately right angles near the north pole 532 and near the south pole 532. As the coil 524 rotates about the z-axis, a current i is induced in the coil. Near the south pole 532', the current i is aligned with the positive z-axis whereas near the north pole 532, the current i is in the opposite direction. As shown in the top view (x-y plane), the current i near the south pole 532' is out-of-the-page (•) while it is in-to-the-page (+) near the north pole 532. However, when the coil 524 rotates (e.g., counterclockwise), the current i in the coil changes direction as the coil 524 rotates.

A variety of schemes are suitable to extract current from the exemplary generator 520. For example, a pair of "brushes" may be used to extract a substantially direct current wherein one brush always has a positive potential relative to another brush. Such brushes or contacts may contact the coil from the side or from the top. Of course, a variety of other schemes are also possible for extracting-direct and/or alternating currents. Such schemes optionally use capacitors or the like.

Figure 6:
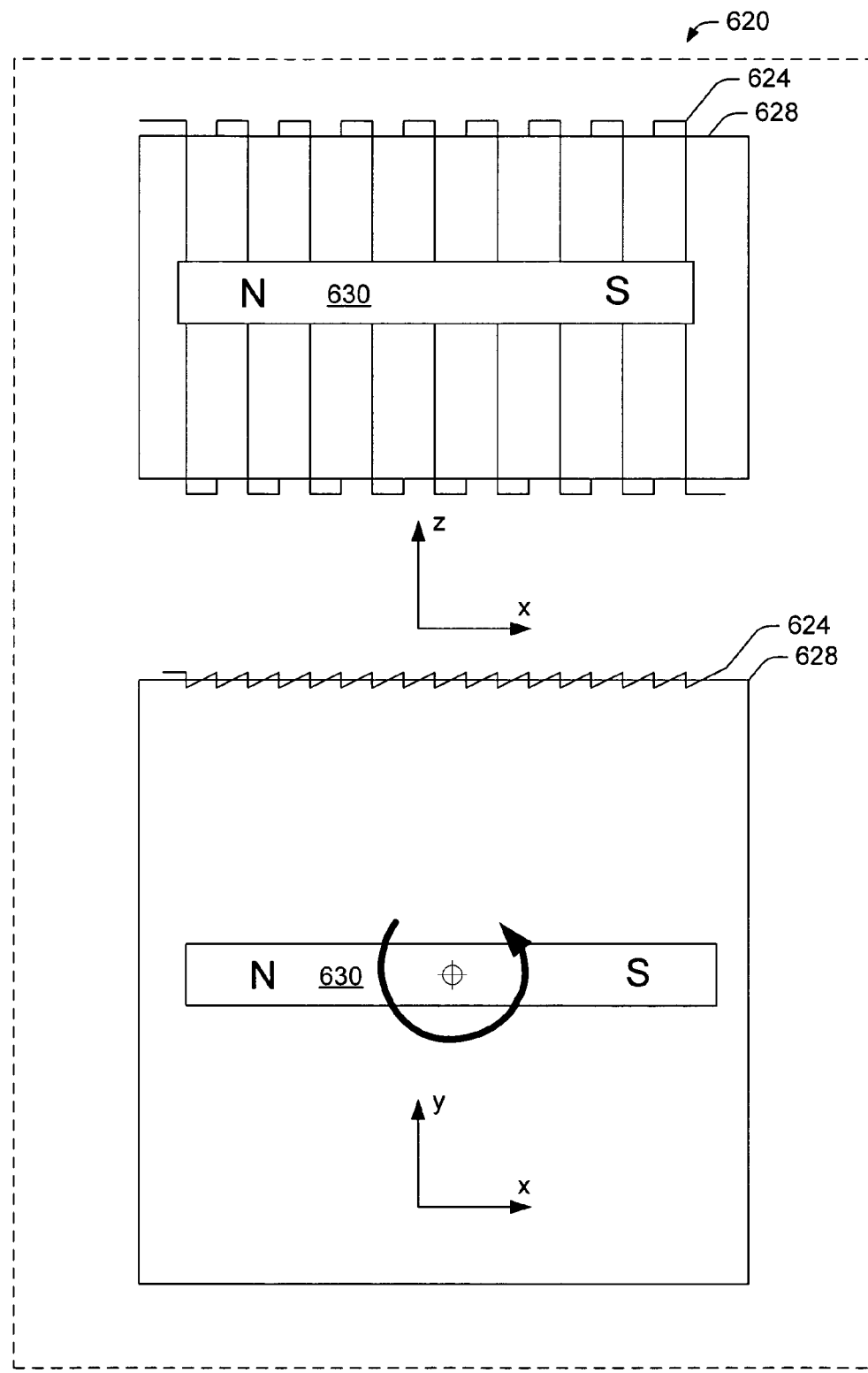
FIG. 6 is an approximately diagram of a rotating magnet generator for use with a biomotor.

Referring to FIG. 6, a side view (e.g., z-x plane) and a top view (e.g., x-y plane) of another exemplary generator 620 are shown. Both views include a coil 624 and a magnet 630 having a north pole and a south pole. According to this exemplary generator 620, the coil 624 serves as a stator while the dipole magnet 630 serves as the rotor. Further, as shown, the coil 624 is wound around a core 628. Of course, an exemplary coil is optionally imprinted, etched, etc. on a material. According to the exemplary generator 620, an emf is induced in the coil 624 upon rotation of the magnet 630 (e.g., see x-y plane view).

Figure 7:
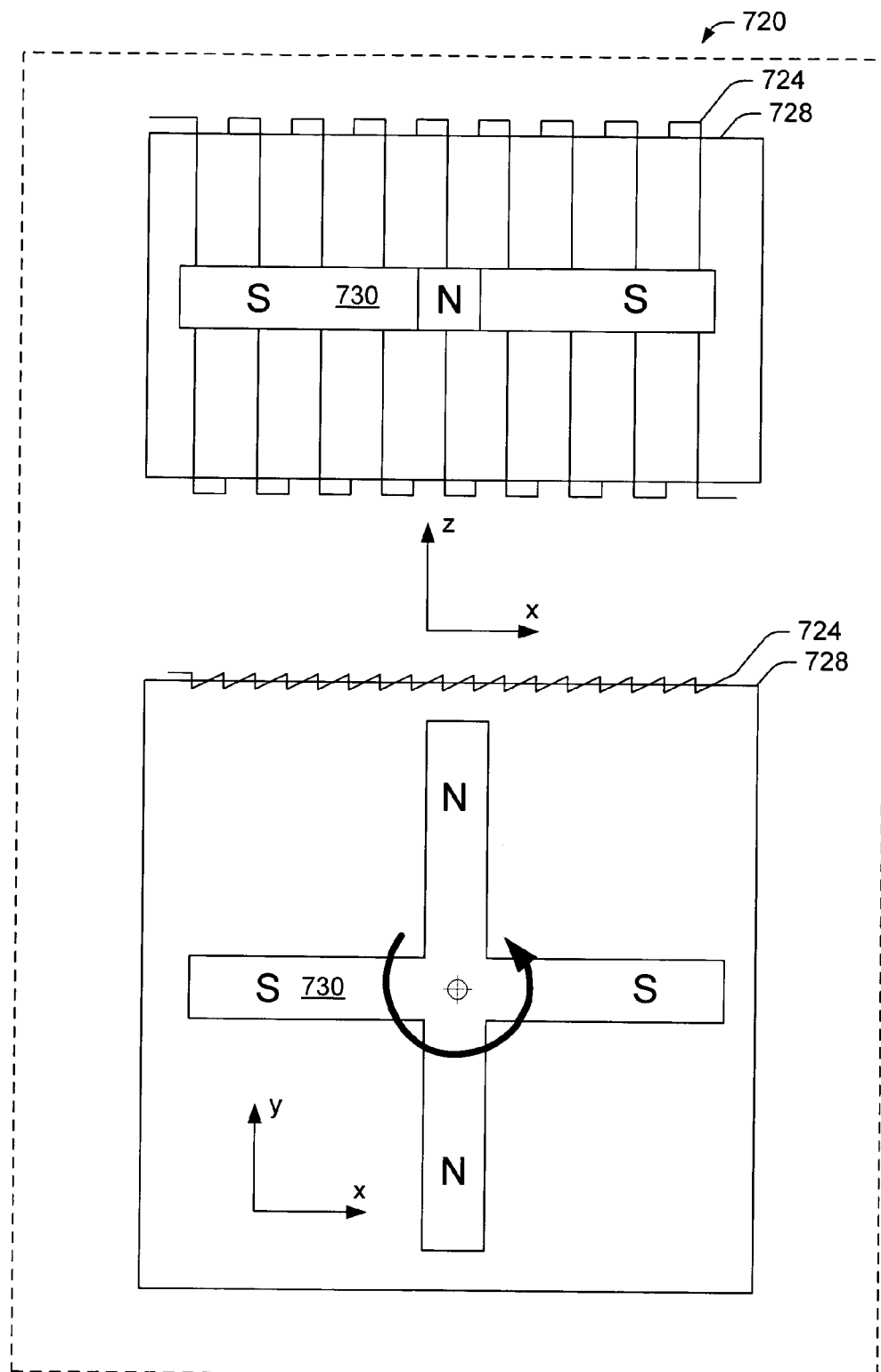
FIG. 7 is an approximate diagram of a rotating magnet generator for use with a biomotor having more than one pair of poles.

A side view (e.g., z-x plane) and a top view (e.g., x-y plane) of yet another exemplary generator 720 are shown in FIG. 7. Both views include a coil stator 724 and a magnet rotor 730 having two north poles and two south poles. Further, as shown, the coil 724 is wound around a core 728. Of course, an exemplary coil is optionally imprinted, etched, etc. on a material. According to the exemplary generator 720, an emf is induced in the coil 724 upon rotation of the magnet rotor 730 (e.g., see x-y plane view). While the magnet rotor 730 has two north poles and two south poles, rotors having additional poles are also optionally suitable for use in a generator.

Figure 8:
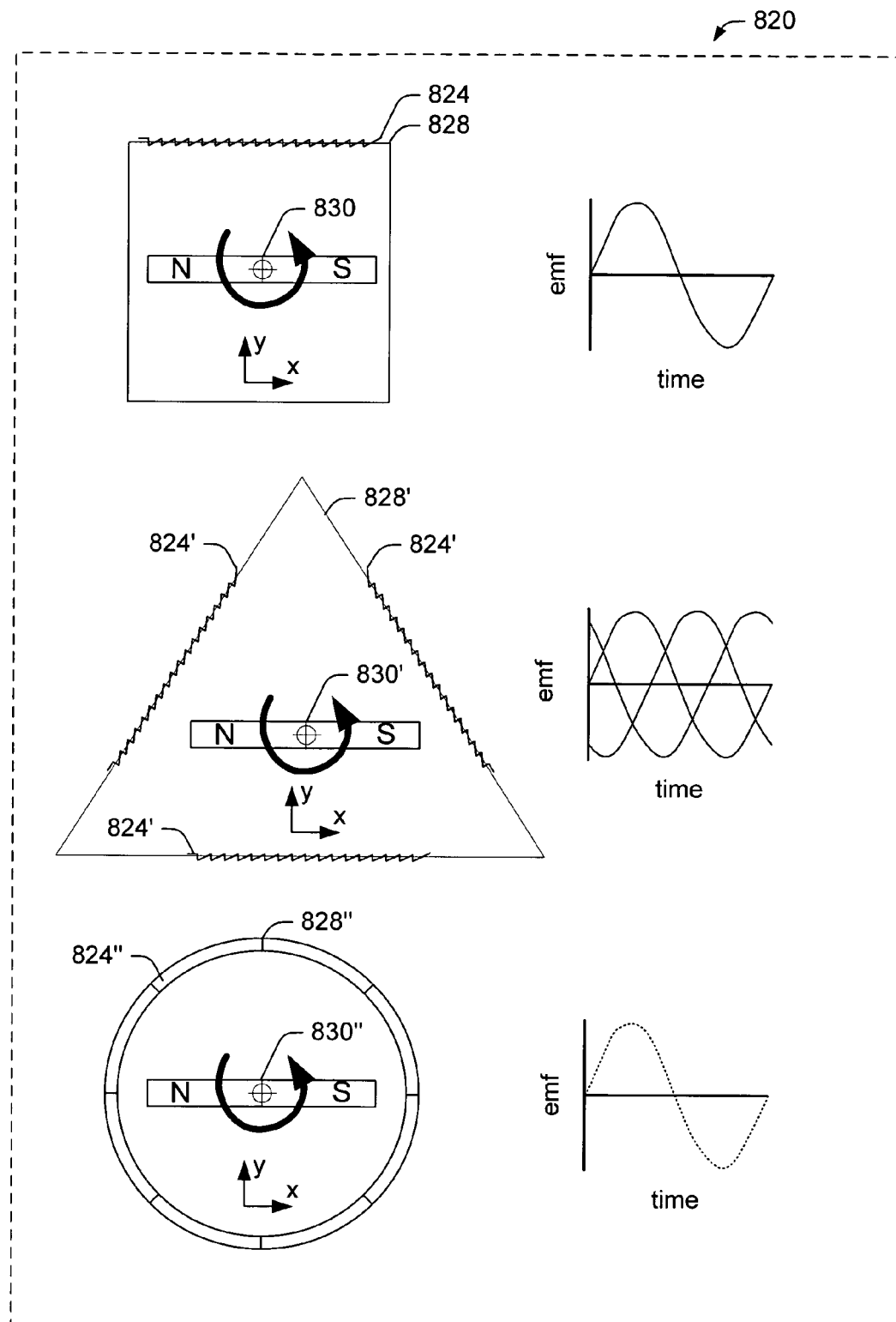
FIG. 8 is an approximate diagram of various stator configurations for a rotating generator.

Referring to FIG. 8, three exemplary generator configurations 820 are shown. The top configuration 822 has a square core, the middle configuration 822' has a triangular core and the bottom configuration 822" has a circular core. The number of coils and the position of the coils in these three configurations 822, 822', 822" are exemplary only as other configurations are possible. In addition, the magnets 830, 830', 830" are optionally permanent and/or electric magnets. are The top configuration 822 is the same as the configuration 620 of FIG. 6. A corresponding plot of emf versus time is also shown for this configuration 822, which is substantially sinusoidal in shape given a constant rotor speed and referred to herein as a single-phase generator. The middle configuration 822' has three coils 824' positioned at approximately 120° intervals on a core 828. As the rotor 830' rotates, emfs induced in three coils 824' are out-of-phase by approximately 120°. This configuration 820' is referred to herein as a three-phase generator. Various electrical connections are possible for linking emfs in a three-phase generator and include "delta" and "wye" connections. In a delta connection, the positive end of each coil is connected to the negative end of an adjacent coil. In a wye connection, all positive ends are connected and a neutral terminal is connected to the positive ends. The negative ends are generally connected to individual negative terminal wires.

Figure 9:
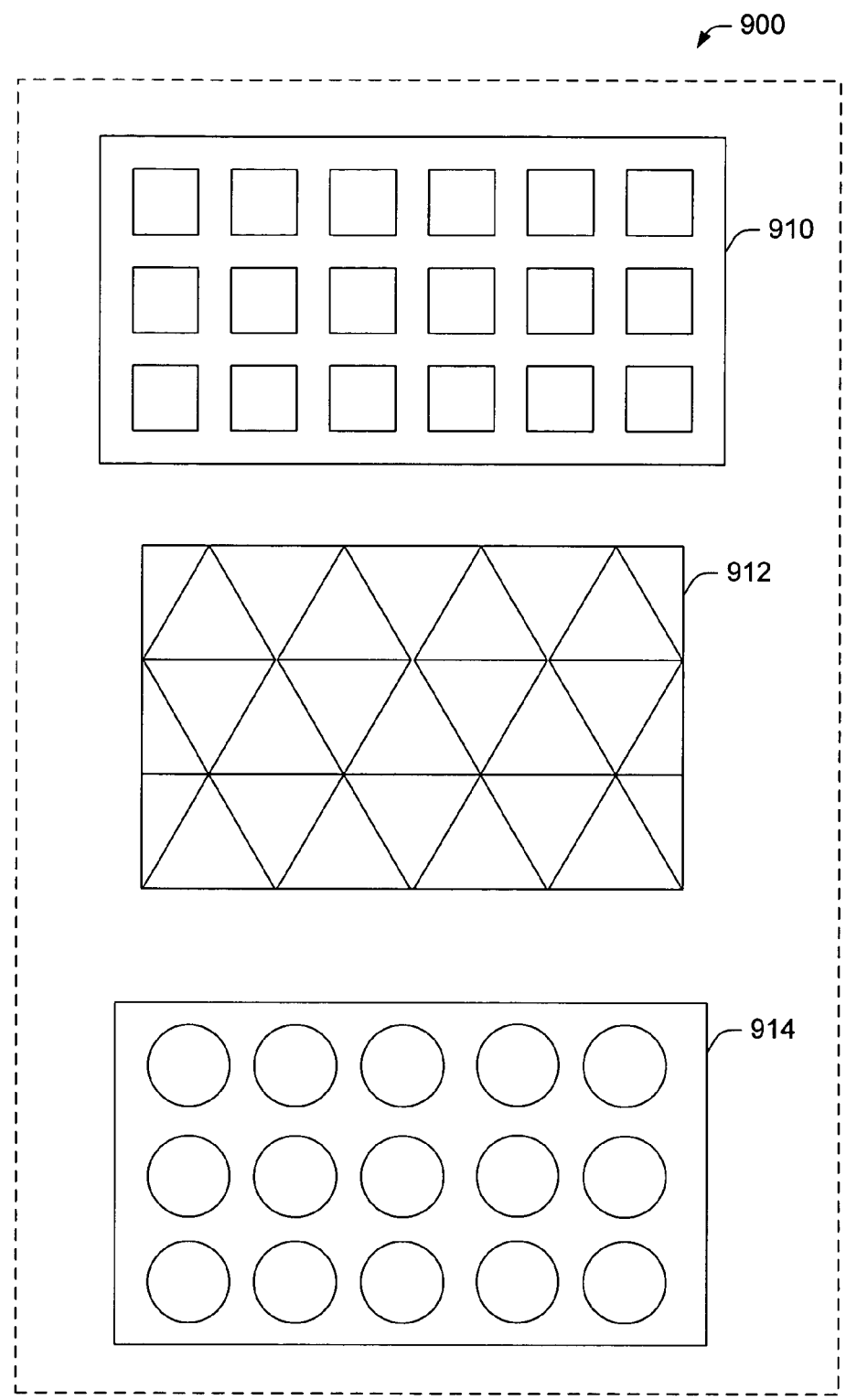
FIG. 9 is an approximate diagram of various biogenerator cell configurations.
Figure 10:
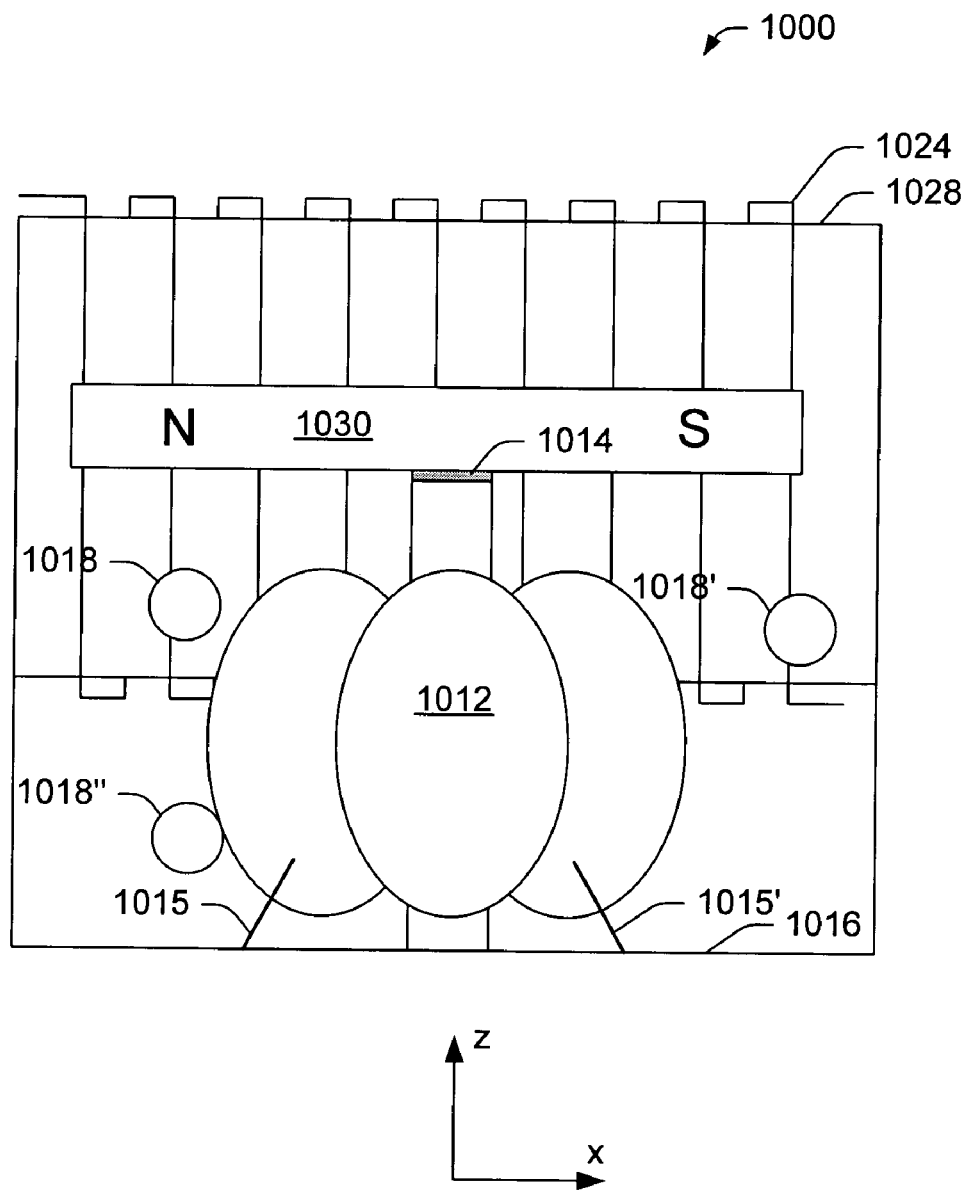
FIG. 10 is an approximate diagram of an exemplary biogenerator having a rotating magnet generator.

Referring to FIG. 9, various exemplary systems of biogenerators 900 are shown. The exemplary system 910 includes a plurality of rectangular-walled cells, the exemplary system 912 includes a plurality of triangular-walled cells and the exemplary system 914 includes a plurality of circular-walled cells. The individual cells in the systems 910, 912, 914 include a biomotor portion and an electric generator portion. For example, referring to FIG. 10, a side view of an exemplary cell 1000 is shown. The cell 1000 includes biomotor components of the biomotor 410 of FIG. 4 and generator components of the generator 620 of FIG. 6. More specifically, the biomotor includes biomolecules 1012, a cap 1014, tags 1015, 1015', a support 1016, and various bioenergy sources 1018, 1018', 1018". The generator includes a coil 1024, a core 1028 and a magnet rotor 1030. Of course, the core 1028 and/or coil 1024 are optionally integral with a cell wall. In addition, an aqueous layer may rise from the support 1016 to any level along the z-axis, for example, to the top of the biomolecules 1012. Further, the coil 1024 and/or core 1028 are optionally electrically insulated but not magnetically insulated from the aqueous layer. Such insulation may prevent electrical short circuits and/or prevent corrosion/chemical reaction between aqueous components and a coil and/or a core.

Figure 11:
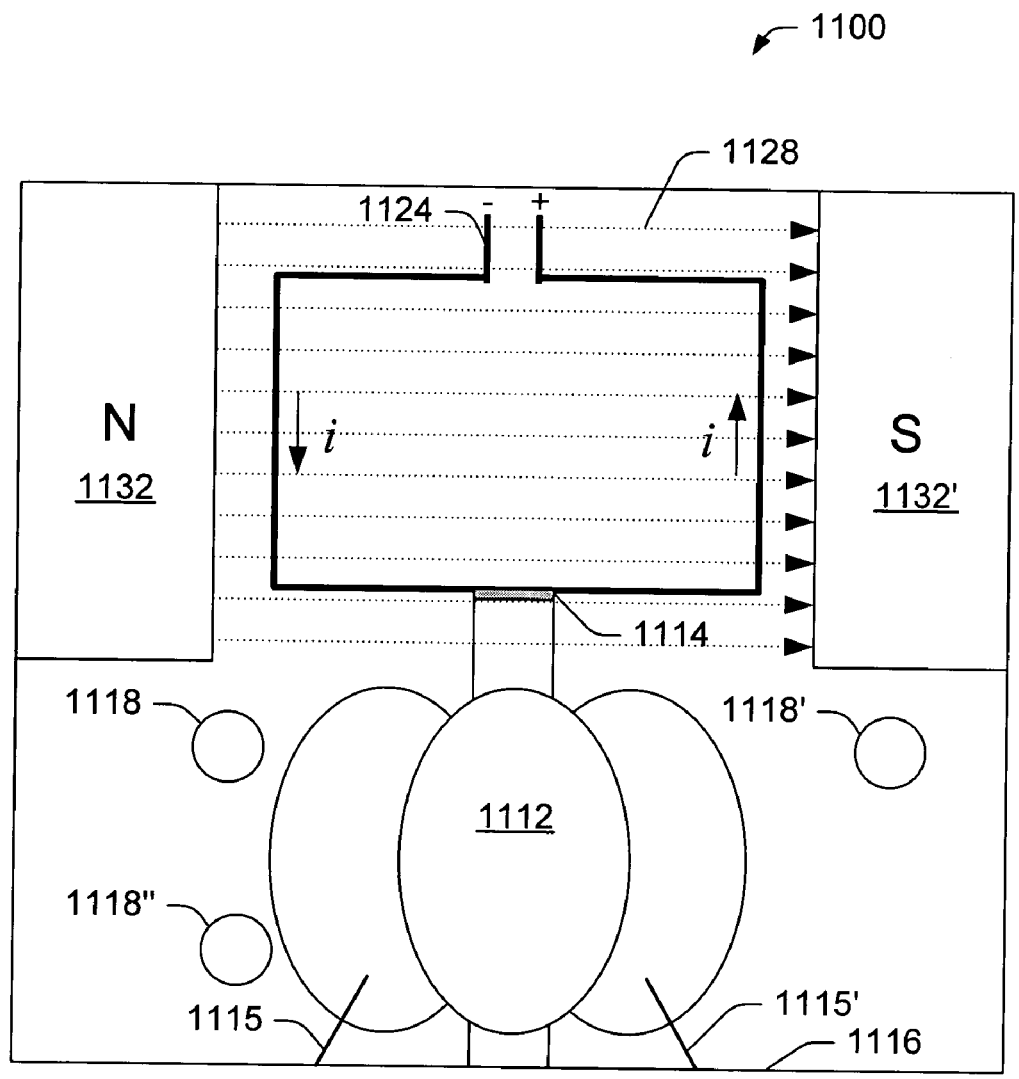
FIG. 11 is an approximate diagram of an exemplary biogenerator having a rotating coil generator.

Referring to FIG. 11, a side view of another exemplary cell 1100 is shown. The cell 1100 includes biomotor components of the biomotor 410 of FIG. 4 and generator components of the generator 520 of FIG. 5. More specifically, the biomotor includes biomolecules 1112, a cap 1114, tags 1115, 1115', a support 1116, and various bioenergy sources 1118, 1118', 1118". The generator includes a coil 1124 and a magnetic field 1128 associated with a magnetic north pole 1132 and a magnetic south pole 1132'. Of course, the magnetic north pole 1132 and/or the magnetic south pole 1132' are optionally integral with a cell wall. In addition, an aqueous layer may rise from the support 1116 to any level along the z-axis, for example, to the top of the biomolecules 1112. Further, the magnetic north pole 1132 and the magnetic south pole 1132' and/or the coil 1124 are optionally electrically insulated but not magnetically insulated from the aqueous layer. Such insulation may prevent electrical short circuits and/or prevent corrosion/chemical reaction between aqueous components and a coil and/or a magnet.

Exemplary Implantable Device with a Biogenerator System

Figure 12:
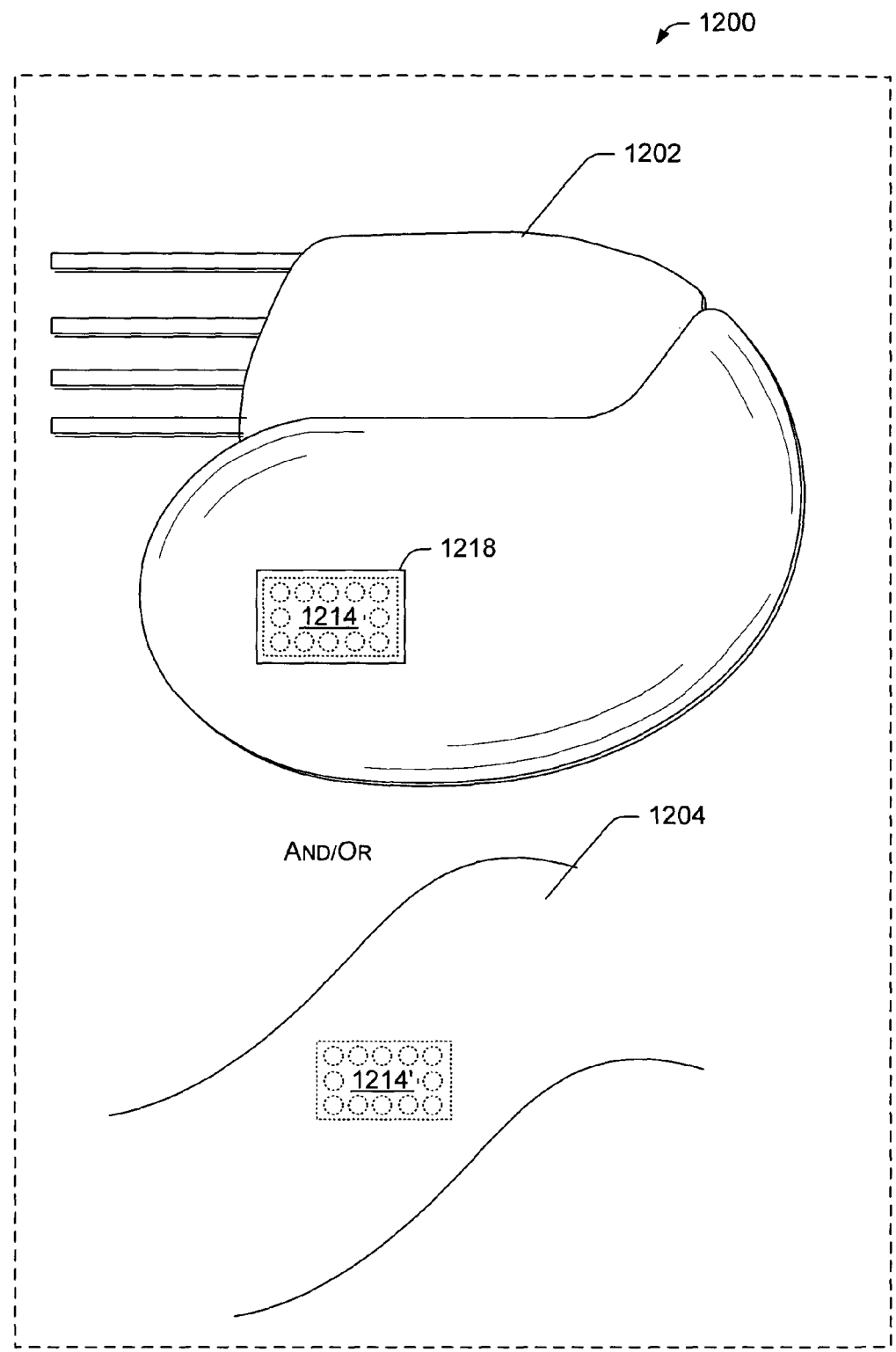
FIG. 12 is an approximate diagram of an implantable device having one or more biogenerators.

Referring to FIG. 12, an approximate diagram 1200 of exemplary biogenerator systems 1214, 1214 are shown in relation to an exemplary implantable stimulation device 1202 and tissue 1204. The stimulation device 1202 optionally includes various components of the exemplary device 100 of FIG. 1 and FIG. 2. In general, the biogenerator system 1214 includes one or more circuits that join cells to thereby provide an output emf. Such output is optionally directed to a storage device (e.g., battery, capacitor, etc.) In addition, the biogenerator 1214 optionally has a permeable layer 1218 that allows for influx and/or efflux of bioenergy sources (e.g., ATP, etc.). Of course, an exemplary biogenerator or biogenerator system (e.g., systems 912, 914, 916 of FIG. 9) may be considered an implantable device.

While the exemplary biogenerator system 1214 is shown as part of a larger implantable device 1202, various exemplary biogenerators and/or biogenerator systems are suitable for implantation in and/or near tissue. Such exemplary biogenerators and/or biogenerator systems optionally deliver stimulation pulses locally to tissue, for example, to nerve and/or muscle tissue. For example, the exemplary biogenerator system 1214' has dimensions suitable for implantation in tissue 1204 (e.g., of the autonomic nervous system, the heart, etc.). Such a system optionally includes use of a membrane and/or other permeable surface. Electricity is optionally delivered directly to tissue from one or more coils. Such an exemplary biogenerator system may optionally act as a node (e.g., SA or AV node) to affect and/or control heart rhythm.

Exemplary Method

Figure 13:
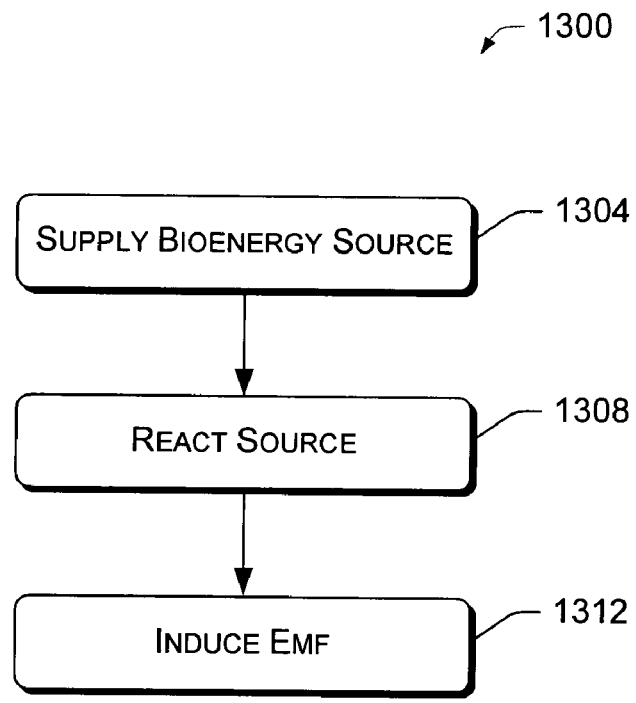
FIG. 13 is a block diagram of an exemplary method for inducing an emf using a biogenerator.

An exemplary method 1300 for inducing an emf is shown in FIG. 13. In a supply block 1304, a biomotor is supplied with a bioenergy source, for example, ATP Next, in a react block 1308, the bioenergy source reacts with the biomotor, for example, ATP is hydrolyzed by F1-ATPase. In an induction block 1312, the biomotor causes a coil and/or a magnet to rotate (and/or translate) and thereby induce an emf in the coil and/or in another coil. According to the exemplary method 1300, the emf may charge a battery and/or capacitor and/or be used for another function related to an implantable stimulation device and/or other implantable device. In one exemplary method, a human body supplies the bioenergy source.

Although exemplary methods, systems and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, systems and/or devices.

What is claimed is:

1. A method for generating an electromagnetic force in an implantable device comprising:
   providing a bioenergy source; and
   reacting the bioenergy source with one or more biological molecules to cause at least one of rotation and translation of a magnet to thereby induce an electromagnetic force in a coil positioned proximate to the magnet.

2. The method of claim 1, wherein the bioenergy source is ATP.

3. The method of claim 1, wherein the biological molecule is an enzyme.

4. The method of claim 3, wherein the enzyme is F1-ATPase.

5. A method for generating an electromagnetic force in an implantable device comprising:
   providing a bioenergy source; and
   reacting the bioenergy source with one or more biological molecules to cause at least one of rotation and translation of a coil in a magnetic field to thereby induce an electromagnetic force in the coil.

6. The method of claim 5, wherein the bioenergy source is ATP.

7. The method of claim 5, wherein the biological molecule is an enzyme.

8. The method of claim 7, wherein the enzyme is F1-ATPase.

9. A biogenerator, capable of generating an electromagnetic force, comprising:
- a generator comprising a coil and a magnet, wherein the coil and magnet are displaceable relative to each other to induce an electromagnetic force in the coil; and
- a biomolecularmotor coupled to the generator, comprising a bioenergy source, and operative to cause a reaction to occur between the bioenergy source and one or more biological molecules to control the generator.

10. The biogenerator of claim 9, wherein the generator comprises a rotating coil generator.

11. The biogenerator of claim 9, wherein the generator comprises a rotating magnet generator.

12. The biogenerator of claim 9, wherein the biomotor comprises an enzyme.

13. The biogenerator of claim 12, wherein the enzyme comprises an enzyme selected from the group comprising kinesin, RNA polymerase, myosin, adenosine triphosphate synthase and/or genetically modified variants thereof.

14. The biogenerator of claim 12, wherein the enzyme comprises F1-ATPase.

15. A method for controlling head function comprising:
- implanting a biogenerator in tissue;
- supplying the biogenerator with a bioenergy source by reacting the bioenergy source with one or more biological molecules;
- generating electricity using the biogenerator and the bioenergy source; and
- stimulating cardiac tissue using the electricity.

16. The method of claim 15, wherein the bioenergy source is ATP.

17. The method of claim 15, wherein the biological molecule is an enzyme.

18. The method of claim 17, wherein the enzyme is F1-ATPase.

19. The method of claim 15, wherein the enzyme comprises an enzyme selected from the group comprising kinesin, RNA polymerase, myosin, adenosine triphosphate synthase and/or genetically modified variants thereof.

* * * * *